(12) United States Patent
Kim et al.

(10) Patent No.: US 8,906,395 B2
(45) Date of Patent: Dec. 9, 2014

(54) PHARMACEUTICAL COMPOSITION IN WHICH SOLUBILITY OF PARTIALLY SOLUBLE TRICYCLIC DERIVATIVE IS IMPROVED

(75) Inventors: Myung-Hwa Kim, Yongin-si (KR); Kwang-Woo Chun, Yongin-si (KR); In-Hae Ye, Anyang-si (KR); Jong-Hee Choi, Suwon-si (KR)

(73) Assignee: Jeil Pharmaceutical Co., Ltd., Seoul (KR)

( * ) Notice: Subject to any disclaimer, the term of this patent is extended or adjusted under 35 U.S.C. 154(b) by 0 days.

(21) Appl. No.: 13/806,837

(22) PCT Filed: Jun. 23, 2011

(86) PCT No.: PCT/KR2011/004600
§ 371 (c)(1),
(2), (4) Date: Dec. 24, 2012

(87) PCT Pub. No.: WO2011/162560
PCT Pub. Date: Dec. 29, 2011

(65) Prior Publication Data
US 2013/0101647 A1    Apr. 25, 2013

(30) Foreign Application Priority Data

Jun. 25, 2010 (KR) .................. 10-2010-0060720
Jun. 21, 2011 (KR) .................. 10-2011-0060003

(51) Int. Cl.
| A61K 47/28 | (2006.01) |
| A61K 9/127 | (2006.01) |
| A61K 9/51  | (2006.01) |
| A61K 9/00  | (2006.01) |
| A61K 31/01 | (2006.01) |
| A61K 31/66 | (2006.01) |

(52) U.S. Cl.
CPC .............. *A61K 47/28* (2013.01); *A61K 9/5123* (2013.01); *A61K 9/0019* (2013.01); *A61K 31/01* (2013.01); *A61K 31/66* (2013.01)
USPC ............................ 424/400; 514/619; 424/450

(58) Field of Classification Search
CPC ...... A61K 47/28; A61K 9/0019; A61K 31/66; A61K 31/01
USPC ........................................... 424/400; 514/619
See application file for complete search history.

(56) References Cited

U.S. PATENT DOCUMENTS

| 5,439,685 A | 8/1995 | Augros |
| 5,560,933 A | 10/1996 | Soon-Shiong et al. |
| 6,080,739 A | 6/2000 | Bombardelli |
| 2004/0247660 A1* | 12/2004 | Singh ........................ 424/450 |
| 2007/0179143 A1* | 8/2007 | Kim et al. ................ 514/247 |

FOREIGN PATENT DOCUMENTS

| KR | 10-2001-0030599 B1 | 4/2007 |
| WO | WO99/13816 A2 | 3/1999 |

OTHER PUBLICATIONS

Szoka Jr.;Title: Comparative properties and methods of preparation of lipid vesicles (Liposomes); Ann. Res. Biophys.; vol. 9; pp. 467-508, 1980.*
International Search Report for PCT/KR2011/004600, ISR published Mar. 5, 2012.

* cited by examiner

*Primary Examiner* — Richard Schnizer
*Assistant Examiner* — Yanzhi Zhang
(74) *Attorney, Agent, or Firm* — The PL Law Group, PLLC (57) ABSTRACT

A pharmaceutical composition includes lipid nanoparticles which include two or more of a phospholipid, cholesterol, and an ionic lipid, and a tricyclic derivative, wherein the solubility of the tricyclic derivative is improved. It is possible to solubilize a partially soluble tricyclic derivative in a high concentration even without using a solubilization aid harmful to the human body, to maintain improved solubility even if water is added for the use as an injection, and to show stability even if stored for a long time, by preparing lipid nanoparticles. Therefore, the lipid nanoparticles of the present invention can be used for preparing a pharmaceutical preparation containing a partially soluble tricyclic derivative as an active ingredient.

14 Claims, 6 Drawing Sheets

PHARMACEUTICAL COMPOSITION IN WHICH SOLUBILITY OF PARTIALLY SOLUBLE TRICYCLIC DERIVATIVE IS IMPROVED

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2011/004600, filed Jun. 23, 2011, which claims priority to Korean Patent Application Nos. 10-2010-0060720, filed Jun. 25, 2010, and 10-2011-0060003, filed Jun. 21, 2011, entire contents of which are incorporated herein by reference.

BACKGROUND

1. Field of the Invention a. The present invention relates to a pharmaceutical composition having improved solubility, which includes lipid nanoparticles comprised of a lipid mixture of phospholipid, cholesterol and ionic lipid; and a tricyclic derivative compound, and to a method for preparing the lipid nanoparticles.

2. Description of the Related Art

Korean Patent Registration No. 10-0667464-0000 discloses a tricyclic derivative compound of Formula 1 as shown below. The compound of Formula 1 that is a colchicine derivative exhibits a very strong cytotoxicity against cancer cell lines, shows a significantly reduced toxicity compared to a colchicine or taxol injection in an animal toxicity test, significantly reduces the tumor size and weight, and shows strong angiogenesis inhibitory activity in HUVEC cells. Thus, the compound of Formula 1 is clinically useful as an anticancer agent, a proliferation inhibitor and an angiogenesis inhibitor. However, the tricyclic derivative compound of Formula 1 has a very low solubility in an aqueous phase, and thus has low bioavailability in an aqueous phase for drug preparation, such as sterile water, water for injection, deionized water or a buffer solvent or is released in body fluids and tissues immediately after administration in vivo even when it is administered as a solubilized pharmaceutical composition. For this reason, the development of a stable pharmaceutical formulation including the compound of Formula 1 has been limited.

In order to solubilize the tricyclic derivative compound of Formula 1 in an aqueous phase, solubilizing agents such as dimethyl sulfoxide, Tween 80 or cremophor should be used. These solubilizing agents, particularly cremophor, are known to cause serious allergic reactions as side effects on the human body.

[Formula 1]

There have been disclosed various technologies for solubilizing drugs having low solubility, including nanoparticles, solid dispersions and micelles.

When insoluble hydrolysable compounds are incorporated into lipid aggregates such as liposomes or micelles, the compounds can be administered under clinical conditions. Liposomes are known as biodegradable delivery systems which are physiologically compatible with a wide range of drugs. In addition, because liposomes eliminate the need for solubilization in an aqueous phase, an insoluble compound can be more concentrated than a single free state and can be easily formulated in liposomes, and thus the drug can be delivered to a target site at high concentration.

U.S. Pat. Nos. 5,439,686 and 5,560,933 disclose the preparation of formulations in which paclitaxel is stably dispersed with albumin microparticles. However, these formulations have a problem in that the effect of paclitaxel is reduced due to the adsorption of serum albumin of the paclitaxel-loaded albumin as compared to conventional formulations prepared using surfactants.

Moreover, Korean Patent Laid-Open Publication No. 1999-0069033 discloses a technology of solubilizing a diterpenoid alkaloid drug using an amphiphilic block copolymer including polylactide or polyglycolide as a biodegradable hydrophobic polymer and polyethylene glycol as a hydrophilic polymer. This technology is effective for drug solubilization and a decrease in the toxicity of the solubilized formulation, but has a shortcoming in that, because the structure of micelles is unstable upon administration in vivo, the core-micelle shell structure is easily broken so that the encapsulated drug is released.

In addition, Korean Patent Laid-Open Publication No. 2001-0030599 discloses a formulation including camptothecin encapsulated in liposome and a preparation method thereof. The formulation includes one or more liposomes including phospholipid and camptothecin, and this liposome formulation has improved pharmacokinetics and stability. However, the technology of encapsulating a drug in liposomes is not suitable for the preparation of a high-concentration drug solution, because the amount of the drug encapsulated in unit liposome is small.

As described above, for the development of a pharmaceutical formulation in which the tricyclic derivative compound of Formula 1, which has low solubility in an aqueous medium, is solubilized at high concentration, there is an urgent demand for a technology that enables the tricyclic derivative compound to be stably contained in structures and allows the compound-containing structures to be stably dispersed in an aqueous phase, thereby solubilizing the poorly soluble drug in the aqueous phase. In addition, there is a need for the development of nanostructures for solubilization of the tricyclic derivative compound, in which the nanostructures have excellent in vivo stability so that they are not easily broken by in vivo components, including body fluids, proteins and salts, upon administration in vivo, and thus the drug is not librated or released from the nanostructures after administration in vivo.

Accordingly, the present inventors have found that, when lipid nanoparticles are prepared by introducing a lipid mixture to a poorly tricyclic derivative compound, the solubility of the tricyclic derivative compound is improved without having to use a solubilizing agent harmful to the human body, and the improved solubility is maintained even when water is added to the lipid nanoparticles in order to form an injectable formulation, and also the prepared solid-state lipid nanoparticles have long-term storage stability, thereby completing the present invention.

Throughout this application, several patents and publications are referenced and citations are provided in parentheses. The disclosure of these patents and publications is incorporated into this application in order to more fully describe this invention and the state of the art to which this invention pertains.

SUMMARY

It is an object of the present invention to provide a pharmaceutical composition having improved solubility, which includes lipid nanoparticles comprised of a poorly soluble tricyclic derivative compound and a lipid mixture.

Another object of the present invention is to provide a method for preparation of lipid nanoparticles which are included in the pharmaceutical composition.

To achieve the above objects, the present invention provides a pharmaceutical composition including lipid nanoparticles comprised of: a lipid mixture of two or more selected from the group consisting of phospholipid, cholesterol and ionic lipid; and a poorly soluble tricyclic derivative compound represented by the following Formula 1:

[Formula 1]

The present invention also provides a method for preparing the pharmaceutical composition, the method including the steps of: (1) dissolving in an organic solvent a lipid mixture of two or more selected from the group consisting of phospholipid, cholesterol and ionic lipid to prepare a lipid mixture solution; (2) dissolving a tricyclic derivative compound of Formula 1 in the lipid mixture solution prepared in step (1); (3) mixing the tricyclic derivative compound-containing lipid mixture solution prepared in step (2) with water while irradiating the mixture with ultrasonic waves, thereby preparing a dispersed lipid nanoparticle solution; (4) vacuum-distilling the lipid nanoparticle solution, prepared in step (3), to remove the organic solvent; and (5) freeze-drying the lipid nanoparticle solution prepared in step (4).

DETAILED DESCRIPTION

As used herein, the term "lipid nanoparticles" refers to nanoparticles comprised of a lipid mixture of two or more of phospholipid, cholesterol and ionic lipid and a tricyclic derivative compound represented by the following Formula 1.

Hereinafter, embodiments of the present invention will be described in detail.

The present invention provides a pharmaceutical composition including lipid nanoparticles comprised of: a lipid mixture of two or more selected from the group consisting of phospholipid, cholesterol and ionic lipid; and a poorly soluble tricyclic derivative compound represented by the following Formula 1, wherein the tricyclic derivative compound has improved solubility:

[Formula 1]

In the lipid mixture, the phospholipid may be any phospholipid or a combination of phospholipids capable of forming liposomes. For example, the phospholipid that is used in the present invention may be suitably selected from among phosphatidylcholines (PCs), including the natural phospholipids obtained from eggs, soybeans or other plant sources, semi-synthetic phospholipids or synthetic phospholipids, phospholipids having various lipid chain lengths, unsaturated phospholipids, and so on. Specifically, the phospholipid that is used in the present invention may be any one or a mixture of two or more selected from among distearoyl phosphatidylcholine (DSPC), hydrogenated soy phosphatidylcholine (HSPC), soy phosphatidylcholine (PC), egg phosphatidylcholine (PC), hydrogenated egg phosphatidylcholine (HEPC), dipalmitoylphosphatidylcholine (DPPC), and dimyristoylphosphatidylcholine (DMPC). Among them, hydrogenated soy phosphatidylcholine (HSPC) is preferably used.

In the lipid mixture, the ionic lipid may be anionic lipid or cationic lipid.

The anionic lipid may be any one or a mixture of two or more selected from among dimyristoyl phosphatidylglycerol (DMPG), dilauryl phosphatidylglycerol (DLPG), dipalmitoyl phosphatidylglycerol (DPPG), distearoyl phosphatidylglycerol (DSPG), dimyristoyl phosphatidic acid (DMPA), distearoyl phosphatidic acid (DSPA), dilauryl phosphatidic acid (DLPA), and dipalmitoyl phosphatidic acid (DPPA). Among them, dipalmitoyl phosphatidic acid (DPPA) is preferably used.

The cationic lipid may be any one or a mixture of two or more selected from among dioleoyl trimethylammonium propane (DOTAP), dimethyloctylamine (DMOA), dioleoyl phosphatidyl ethanolamine (DOPE), dialkyl dimethyl ammonium bromide (DXDAB), and dialkyl trimethyl ammonium propane (DXTAP).

Among the constituent components of the lipid mixture according to an embodiment of the present invention, the phospholipid serves to form the structure of the lipid nanoparticles, the cholesterol serves to stabilize the structure of the lipid nanoparticles, and the ionic lipid serves to prevent the lipid nanoparticles from agglomerating with each other.

In the lipid mixture according to an embodiment of the present invention, the ratio of phospholipid:cholesterol:ionic lipid is preferably 0-100:0-20:0-10 parts by weight, more preferably 0-20:0-7:1-3 parts by weight, and even more preferably 7:3:1 parts by weight.

If the ratio of the phospholipid is more than 100 parts by weight, or if the ratio of the cholesterol is more than 20 parts by weight, or if the ratio of the ionic lipid is more than 10, the size of the particles will excessively increase.

In addition, the ratio of the lipid mixture (comprised of phospholipid, cholesterol and ionic lipid) to the tricyclic derivative compound is preferably 1-20:1 parts by weight, and more preferably 3:1. If the ratio of the lipid mixture to the tricyclic derivative compound is less than 1 part by weight, the size of the lipid nanoparticles will increase, and the release of the compound from the lipid nanoparticles will occur, suggesting that improvement in the solubility of the compound is insufficient. On the other hand, if the ratio of the lipid mixture to the tricyclic derivative compound is more than 20, there will be no further improvement in the particle size, and the amount of a solvent for dissolving the lipid mixture will greatly increase to cause problems with processes and to reduce economic efficiency.

Furthermore, the size of the lipid nanoparticles according to an embodiment of the present invention is 1-1,000 nm, and, for example, 20-200 nm. If the size of the lipid nanoparticles is less than 1 nm, the encapsulation efficiency of the drug will decrease, and if the size of the lipid nanoparticles is more than 1000 nm, the lipid nanoparticles will be difficult to use as an injectable formulation.

In addition, the pharmaceutical composition according to an embodiment of the present invention may contain one or more selected from among conventional antioxidants, including ethylenediamine tetraacetate, erythorbic acid, dibutylhydroxytoluene, butylhydroxyanisole, propyl gallate, ascorbic acid, alpha-tocopherol, beta-tocopherol, gamma-tocopherol, and delta-tocopherol.

Further, the pharmaceutical composition according to the present invention may contain a conventional bulking agent for freeze drying, such as sucrose, mannitol or creatine. This bulking agent for freeze drying can prevent the lipid nanoparticles from being agglomerated with each other in the freeze-drying step (step (5)) of the method for preparing the lipid nanoparticles. In addition, the bulking agent for freeze drying enables the prepared solid-state lipid nanoparticles to be dispersed rapidly without re-agglomeration when they are added to water for injection, thereby maintaining the initial size of the lipid nanoparticles.

The present invention also provides a method for preparing the lipid nanoparticles including the tricyclic derivative compound of Formula 1.

Specifically, the present invention provides a method for preparing lipid nanoparticles which are included in a pharmaceutical composition including a tricyclic derivative compound having improved solubility, the method including the steps of:

(1) dissolving in an organic solvent a lipid mixture of two or more selected from the group consisting of phospholipid, cholesterol and ionic lipid to prepare a lipid mixture solution;

(2) dissolving a tricyclic derivative compound of Formula 1 in the lipid mixture solution prepared in step (1);

(3) mixing the tricyclic derivative compound-containing lipid mixture solution prepared in step (2) with water while irradiating the mixture with ultrasonic waves, thereby preparing a dispersed lipid nanoparticle solution;

(4) vacuum-distilling the lipid nanoparticle solution, prepared in step (3), to remove the organic solvent; and (5) freeze-drying the lipid nanoparticle solution prepared in step (4).

Hereinafter, each step of the preparation method according to an embodiment of the present invention will be described in further detail.

In the method for preparing the lipid nanoparticles according to an embodiment of the present invention, step (1) is a step of dissolving a lipid mixture in an organic solvent to prepare a lipid mixture solution. Examples of the organic solvent that is used to dissolve the lipid mixture include chloroform, dichloromethane, methanol, ethanol, acetone, acetonitrile, isopropyl alcohol, tetrahydrofuran and the like.

Herein, the ratio of phospholipid:cholesterol:ionic lipid is preferably 0-100:0-20:0-10 parts by weight, more preferably 0-20:0-7:1-3 parts by weight, and even more preferably 7:3:1 part by weight. The reason why the ratio of phospholipid:cholesterol:ionic lipid is limited is as described above.

Meanwhile, the concentration of the lipid mixture in the lipid mixture solution is preferably in the range of 20 to 200 mg/ml.

In the method for preparing the lipid nanoparticles according to an embodiment of the present invention, step (2) is a step of dissolving the tricyclic derivative solution in the lipid mixture solution obtained in step (1).

In this step, the ratio of lipid mixture: tricyclic derivative compound may be 1-20:1 part by weight, and, for example, 3:1 part by weight.

Meanwhile, the concentration of the tricyclic derivative solution in the lipid mixture solution is, for example, in the range of 20 to 200 mg/ml.

In the method for preparing the lipid nanoparticles according to an embodiment of the present invention, step (3) is a step of obtaining lipid nanoparticles from the lipid mixture solution obtained in step (2). Specifically, in this step, the tricyclic derivative compound-containing lipid mixture solution obtained in step (2) is mixed with water while it is irradiated with ultrasonic waves, thereby preparing a lipid nanoparticle solution containing the lipid mixture dispersed therein.

The dispersed lipid nanoparticle solution can be obtained using 1) a method of adding water to the lipid mixture solution containing the tricyclic derivative compound, 2) a method of adding the lipid mixture solution containing the tricyclic derivative compound to water, or 3) a method of simultaneously adding the tricyclic derivative compound-containing lipid mixture solution and water. Among these methods, method 1) is preferably used, because it can increase the stability of the produced lipid nanoparticles.

Meanwhile, a system for irradiating the mixture with ultrasonic waves is not specifically limited, but a tip sonicator is preferably used.

In the method for preparing the lipid nanoparticles according to an embodiment of the present invention, step (4) is a step of vacuum-distilling the lipid nanoparticle solution obtained in step (3). Specifically, in this step, the dispersed lipid nanoparticle solution obtained in step (3) is vacuum-distilled to remove the organic solvent.

In step (4), filtration and sterilization may further be performed using a membrane having a pore size of 0.1-0.5 μm, for example, 0.2 μm. If the pore size of the membrane is less than 0.1 μm, the lipid nanoparticles cannot pass through the membrane, and if the pore size is more than 0.5 μm, particles having a size unsuitable for injection will pass through the membrane.

Additionally, after vacuum distillation in step (4), a conventional antioxidant or a conventional bulking agent for freeze drying may, if necessary, be added. Examples of the antioxidant include ethylenediamine tetraacetate, erythorbic acid, dibutylhydroxytoluene, butylhydroxyanisole, propyl gallate, ascorbic acid, alpha-tocopherol, beta-tocopherol, gamma-tocopherol, delta-tocopherol, and examples of the bulking agent for freeze drying include sucrose, mannitol and creatine.

In the method for preparing the lipid nanoparticles according to an embodiment of the present invention, step (5) is a step of freeze-drying the lipid nanoparticle solution obtained in step (4), thereby obtaining solid-state lipid nanoparticles as a desired product.

Meanwhile, the solid-state lipid nanoparticles according to an embodiment of the present invention increase the solubility of the tricyclic derivative compound without having to use a solubilizing agent harmful to the human body and maintain the improved solubility of the compound even when water is added thereto to form an injectable formulation.

The prepared solid-state lipid nanoparticles are stable in terms of their appearance and purity even when they are stored for a long period of time. Thus, the solid-state lipid nanoparticles are useful for the preparation of a pharmaceutical formulation containing the tricyclic derivative compound as an active ingredient.

A pharmaceutical composition, which includes the lipid nanoparticles according to the present invention and has improved solubility, can be pharmaceutically formulated in various oral or parenteral dosage forms.

Examples of formulations for oral administration include tablets, pills, soft/hard capsules, liquids, syrups, granules and elixirs. These formulations may contain, in addition to the active ingredient, one or more diluents or excipients, such as fillers, extenders, wetting agents, disintegrants, lubricants, binders or surfactants, which are generally used in the art.

Examples of the disintegrant that may be used in the present invention include agar, starch, alginic acid or its sodium salt, and anhydrous calcium monohydrogen phosphate, and examples of the lubricant that may be used in the present invention include silica, talc, stearic acid or its magnesium salt or calcium salt, and polyethylene glycol. Examples of the binder that may be used in the present invention include magnesium aluminum silicate magnesium aluminum silicate, starch paste, gelatin, tragacanth, methylcellulose, sodium carboxymethylcellulose, polyvinylpyrrolidone, low-substituted hydroxypropylcellulose and the like.

In addition, the pharmaceutical composition of the present invention may contain a diluent such as lactose, dextrose, sucrose, mannitol, sorbitol, cellulose or glycine. In some cases, the pharmaceutical composition may also contain an azeotropic mixture, an absorbent, a coloring agent, a flavoring agent, a sweetening agent and the like, which are generally known in the art.

Moreover, the pharmaceutical composition according to the present invention may be administered by parenteral routes. Formulations for parenteral administration include subcutaneous, intravenous, intramuscular or intrathoracic injections, or transdermal formulations.

To prepare an injectable formulation, the derivative compound of Formula 1 or a pharmaceutically acceptable salt thereof may be mixed with a stabilizer or a buffer in water to prepare a solution or suspension which may then be prepared in the form of an ampule or vial for unit dosage.

In addition, a transdermal formulation can be prepared by storing the derivative compound of Formula 1 or a pharmaceutically acceptable salt thereof in a patch-type drug delivery system including a drug protecting layer, a drug storage layer, a release rate control film and an adhesive.

The pharmaceutical composition may be sterilized or may further contain excipients, including preservatives, stabilizers, salts for control for osmotic pressure and buffers, and other therapeutically useful substances. The pharmaceutical composition can be formulated according to a conventional mixing, granulation or coating method. If necessary, the composition of the present invention may be administered in combination with other drugs, for example, anticancer agents.

When the composition of the present invention is formulated in a unit dosage form, it preferably has the derivative of Formula 1 or a pharmaceutically acceptable salt thereof as an active ingredient at a unit dose of about 0.1-1,500 mg. The dosage of the active ingredient follows a physician's prescription depending on various factors, including the patient's weight, age and disease severity. However, the dosage required for treatment of an adult is usually in the range of about 1 mg/day to about 500 mg/day, depending on the frequency and intensity of administration. In the case of intramuscular or intravenous administration into an adult, about 5 mg to about 300 mg per day may be sufficient as a separate one-time dosage. However, a higher dosage is preferable for some patients.

Hereinafter, the present invention will be described in further detail with reference to examples. It is to be understood, however, that these examples are for illustrative purposes only and are not intended to limit the scope of the present invention.

EXAMPLE 1

Preparation 1 of Lipid Nanoparticles Containing Tricyclic Derivative Compound According to the Present Invention 4.582 g of hydrogenated soy phosphatidylcholine (HSPC), 1.964 g of cholesterol, 0.655 g of dipalmitoyl phosphatidic acid (DPPA) and 14.4 mg of alpha-tocopherol (weight ratio of phospholipid:cholesterol:ionic lipid=7:3:1) were dissolved in a mixed organic solvent of 60 ml of methanol and 40 ml of dichloromethane to prepare a lipid mixture solution. Then, 2.4 g of the tricyclic derivative solution of Formula 1 was dissolved in the prepared lipid mixture solution (weight ratio of lipid mixture: tricyclic derivative compound=3:1).

The lipid mixture solution containing the tricyclic derivative solution was cooled to 0° C., and then 200 ml of distilled water was added at a rate of 25 ml/min while the mixture was irradiated with ultrasonic waves from a tip sonicator (VCX750, Sonics) to disperse the lipid nanoparticles. Then, the lipid mixture solution was vacuum-distilled to remove the organic solvent and was sterilized by filtration through a 0.2 μm membrane.

Next, 28.8 g of sucrose was added to the lipid nanoparticle solution which was then freeze-dried, thereby preparing solid-state lipid nanoparticles containing the tricyclic derivative compound.

Next, 28.8 g of sucrose was added to the sterilized lipid nanoparticles which were then freeze-dried, thereby preparing solid-state lipid nanoparticles containing the tricyclic derivative compound.

EXAMPLE 2

Preparation 2 of Lipid Nanoparticles Containing Tricyclic Derivative Compound According to the Present Invention Lipid nanoparticles containing the tricyclic derivative compound were prepared in the same manner as Example 1, except that the lipid mixture solution containing the tricyclic derivative compound was added to 200 ml of distilled water.

EXAMPLE 3

Preparation 3 of Lipid Nanoparticles Containing Tricyclic Derivative Compound According to the Present Invention Lipid nanoparticles containing the tricyclic derivative compound were prepared in the same manner as Example 1, except that the tricyclic derivative compound-containing lipid mixture solution and 200 ml of distilled water were simultaneously added.

EXAMPLE 4

Preparation 4 of Lipid Nanoparticles Containing Tricyclic Derivative Compound According to the Present Invention Lipid nanoparticles containing the tricyclic derivative compound (weight ratio of lipid mixture solution: tricyclic derivative compound=2:1) were prepared in the same manner as Example 1, except that 3.055 g of hydrogenated soy phosphatidylcholine (HSPC), 1.309 g of cholesterol and 0.436 g of dipalmitoyl phosphatidic acid (DPPA) (weight ratio of phospholipid:cholesterol:ionic lipid=7:3:1) were used.

EXAMPLE 5

Preparation 5 of Lipid Nanoparticles Containing Tricyclic Derivative Compound According to the Present Invention Lipid nanoparticles containing the tricyclic derivative compound (weight ratio of lipid mixture solution: tricyclic derivative compound=1:1) were prepared in the same manner as Example 1, except that 1.527 g of hydrogenated soy phosphatidylcholine, 0.655 g of cholesterol and 0.218 g of dipalmitoyl phosphatidic acid (weight ratio of phospholipid:cholesterol:ionic lipid=7:3:1) were used.

EXAMPLE 6

Preparation 6 of Lipid Nanoparticles Containing Tricyclic Derivative Compound According to the Present Invention Lipid nanoparticles containing the tricyclic derivative compound (weight ratio of lipid mixture solution: tricyclic derivative compound=4:1) were prepared in the same manner as Example 1, except that 180 mg of the tricyclic derivative compound of Formula 1, 458 mg of hydrogenated soy phosphatidylcholine, 196 mg of cholesterol and 65 mg of dipalmitoyl phosphatidic acid (weight ratio of phospholipid:cholesterol:ionic lipid=7:3:1) were used.

EXAMPLE 7

Preparation 7 of Lipid Nanoparticles Containing Tricyclic Derivative Compound According to the Present Invention Lipid nanoparticles containing the tricyclic derivative compound (weight ratio of lipid mixture solution: tricyclic derivative compound=6:1) were prepared in the same manner as Example 1, except that 120 mg of the tricyclic derivative compound of Formula 1, 458 mg of hydrogenated soy phosphatidylcholine, 196 mg of cholesterol and 65 mg of dipalmitoyl phosphatidic acid (weight ratio of phospholipid:cholesterol:ionic lipid=7:3:1) were used.

EXAMPLE 8

Preparation 8 of Lipid Nanoparticles Containing Tricyclic Derivative Compound According to the Present Invention Lipid nanoparticles containing the tricyclic derivative compound (weight ratio of lipid mixture solution: tricyclic derivative compound=10:1) were prepared in the same manner as Example 1, except that 72 mg of the tricyclic derivative compound of Formula 1, 458 mg of hydrogenated soy phosphatidylcholine, 196 mg of cholesterol and 65 mg of dipalmitoyl phosphatidic acid (weight ratio of phospholipid:cholesterol:ionic lipid=7:3:1) were used.

EXAMPLE 9

Preparation 9 of Lipid Nanoparticles Containing Tricyclic Derivative Compound According to the Present Invention Lipid nanoparticles containing the tricyclic derivative compound (weight ratio of lipid mixture solution: tricyclic derivative compound=20:1) were prepared in the same manner as Example 1, except that 36 mg of the tricyclic derivative compound of Formula 1, 458 mg of hydrogenated soy phosphatidylcholine, 196 mg of cholesterol and 65 mg of dipalmitoyl phosphatidic acid (weight ratio of phospholipid:cholesterol:ionic lipid=7:3:1) were used.

EXAMPLE 10

Preparation 10 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 240 mg of the tricyclic derivative compound of Formula 1, 504 mg of hydrogenated soy phosphatidylcholine and 216 mg of cholesterol (weight ratio of phospholipid:cholesterol:ionic lipid=7:3:0) were used.

EXAMPLE 11

Preparation 11 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 72 mg of the tricyclic derivative compound of Formula 1, 162 mg of cholesterol and 54 mg of dipalmitoyl phosphatidic acid (weight ratio of phospholipid:cholesterol:ionic lipid=0:3:1) were used.

EXAMPLE 12

Preparation 12 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 168 mg of the tricyclic derivative compound of Formula 1, 441 mg of hydrogenated soy phosphatidylcholine and 63 mg of dipalmitoyl phosphatidic acid (weight ratio of phospholipid:cholesterol:ionic lipid=7:0:1) were used.

EXAMPLE 13

Preparation 13 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 80 mg of the tricyclic derivative compound of Formula 1, 129 mg of hydrogenated soy phosphatidylcholine, 55 mg of cholesterol and 55 mg of dipalmitoyl phosphatidic acid (weight ratio of phospholipid:cholesterol:ionic lipid=7:3:3) were used.

EXAMPLE 14

Preparation 14 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 48 mg of the tricyclic derivative compound of Formula 1, 67 mg of hydrogenated soy phosphatidylcholine, 29 mg of cholesterol and 48 mg of dipalmitoyl phosphatidic acid (weight ratio of phospholipid:cholesterol:ionic lipid=7:3:5) were used.

EXAMPLE 15

Preparation 15 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 41 mg of the tricyclic derivative compound of Formula 1, 43 mg of hydrogenated soy phosphatidylcholine, 18 mg of cholesterol and 61 mg of dipalmitoyl phosphatidic acid (weight ratio of phospholipid:cholesterol:ionic lipid=7:3:10) were used.

EXAMPLE 16

Preparation 16 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 96 mg of the tricyclic derivative compound of Formula 1, 58 mg of hydrogenated soy phosphatidylcholine, 173 mg of cholesterol and 58 mg of dipalmitoyl phosphatidic acid (weight ratio of phospholipid:cholesterol:ionic lipid=1:3:1) were used.

EXAMPLE 17

Preparation 17 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 144 mg of the tricyclic derivative compound of Formula 1, 185 mg of hydrogenated soy phosphatidylcholine, 185 mg of cholesterol and 62 mg of dipalmitoyl phosphatidic acid (weight ratio of phospholipid:cholesterol:ionic lipid=3:3:1) were used.

EXAMPLE 18

Preparation 18 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 312 mg of the tricyclic derivative compound of Formula 1, 669 mg of hydrogenated soy phosphatidylcholine, 200 mg of cholesterol and 67 mg of dipalmitoyl phosphatidic acid (weight ratio of phospholipid:cholesterol:ionic lipid=10:3:1) were used.

EXAMPLE 19

Preparation 19 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 184 mg of the tricyclic derivative compound of Formula 1, 460 mg of hydrogenated soy phosphatidylcholine, 69 mg of cholesterol and 23 mg of dipalmitoyl phosphatidic acid (weight ratio of phospholipid:cholesterol:ionic lipid=20:3:1) were used.

EXAMPLE 20

Preparation 20 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 176 mg of the tricyclic derivative compound of Formula 1, 466 mg of hydrogenated soy phosphatidylcholine, 46 mg of cholesterol and 16 mg of dipalmitoyl phosphatidic acid (weight ratio of phospholipid:cholesterol:ionic lipid=30:3:1) were used.

EXAMPLE 21

Preparation 21 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 182 mg of the tricyclic derivative compound of Formula 1, 505 mg of hydrogenated soy phosphatidylcholine, 30 mg of cholesterol and 10 mg of dipalmitoyl phosphatidic acid (weight ratio of phospholipid:cholesterol:ionic lipid=50:3:1) were used.

EXAMPLE 22

Preparation 22 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 165 mg of the tricyclic derivative compound of Formula 1, 475 mg of hydrogenated soy phosphatidylcholine, 14 mg of cholesterol and 5 mg of dipalmitoyl phosphatidic acid (weight ratio of phospholipid:cholesterol:ionic lipid=100:3:1) were used.

EXAMPLE 23

Preparation 23 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 192 mg of the tricyclic derivative compound of Formula 1, 448 mg of hydrogenated soy phosphatidylcholine, 64 mg of cholesterol and 64 mg of dipalmitoyl phosphatidic acid (weight ratio of phospholipid:cholesterol:ionic lipid=7:1:1) were used.

EXAMPLE 24

Preparation 24 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 288 mg of the tricyclic derivative compound of Formula 1, 465 mg of hydrogenated soy phosphatidylcholine, 332 mg of cholesterol and 66 mg of dipalmitoyl phosphatidic acid (weight ratio of phospholipid:cholesterol:ionic lipid=7:5:1) were used.

EXAMPLE 25

Preparation 25 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 3368 mg of the tricyclic derivative compound of Formula 1, 470 mg of hydrogenated soy phosphatidylcholine, 470 mg of cholesterol and 67 mg of dipalmitoyl phosphatidic acid (weight ratio of phospholipid:cholesterol:ionic lipid=7:7:1) were used.

EXAMPLE 26

Preparation 26 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 136 mg of the tricyclic derivative compound of Formula 1, 159 mg of hydrogenated soy phosphatidylcholine, 227 mg of cholesterol and 23 mg of dipalmitoyl phosphatidic acid (weight ratio of phospholipid:cholesterol:ionic lipid=7:10:1) were used.

EXAMPLE 27

Preparation 27 of Lipid Nanoparticles Containing Tricyclic Derivative Compound According to the Present Invention Lipid nanoparticles containing the tricyclic derivative compound (weight ratio of lipid mixture solution: tricyclic derivative compound=3:1) were prepared in the same manner as Example 1, except that 118 mg of the tricyclic derivative compound of Formula 1, 88 mg of hydrogenated soy phosphatidylcholine, 253 mg of cholesterol and 13 mg of dipalmitoyl phosphatidic acid (weight ratio of phospholipid:cholesterol:ionic lipid=7:20:1) were used.

COMPARATIVE EXAMPLE 1

Preparation of Lipid Nanoparticles Containing No Tricyclic Derivative Compound According to the Present Invention Lipid nanoparticles were prepared in the same manner as Example 1, except that the tricyclic derivative compound was not added.

REFERENCE EXAMPLE 1

Measurement of Solubility of Tricyclic Derivative Compound in Water

The solubility of the tricyclic derivative compound of Formula 1 in water was measured in the following manner.

Figure 1:
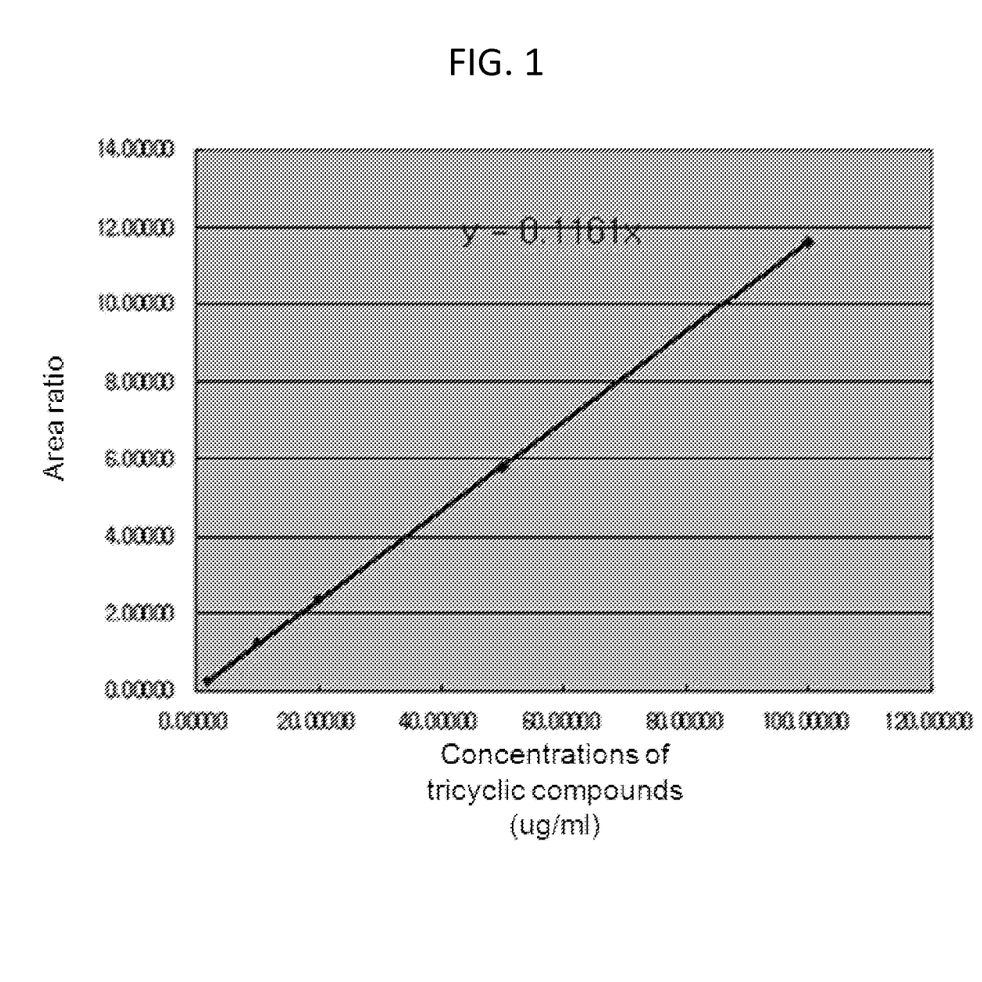
FIG. 1 shows a standard curve obtained by performing HPLC to measure the solubility of a tricyclic derivative compound in an organic solvent.

1.42 mg of the tricyclic derivative compound was dissolved in acetonitrile to prepare 100 μl/ml of a solution which was then serially diluted to prepare 50 μl/ml, 20 μl/ml and 10 μl/ml of standard solutions. 3-ethoxythiocolchicine as an internal standard was added to each of the standard solutions which were then analyzed by HPLC to measure the area ratio of the tricyclic derivative compound. FIG. 1 shows the area ratio of the tricyclic derivative compound as a standard curve.

Then, 1 g of the tricyclic derivative compound was added to 10 ml of distilled water to make a suspension which was then stirred at room temperature for 24 hours to sufficiently dissolve the compound. Then, the suspension was filtered through a 0.2 μm membrane to remove insoluble materials, and the remaining filtrate was analyzed by HPLC using 3-ethoxythiocolchicine as an internal standard to measure the area ratio of the tricyclic derivative compound, which was then compared with the area ratio of the standard curve shown in FIG. 1, thereby determining the concentration of the tricyclic derivative compound dissolved in water.

From the results of the test, it could be seen that the solubility of the tricyclic derivative compound in water was 0.00 μl/ml, suggesting that the tricyclic derivative compound is very poorly soluble in an aqueous phase.

REFERENCE EXAMPLE 2

Measurement of Solubility of Tricyclic Derivative Compound in Solubilizing Agents The solubility of the tricyclic derivative compound in a solubilizing agent was measured in the following manner.

The solubility of the tricyclic derivative compound in various solubilizing agents, which are generally used in injectable formulations, were measured in the same manner as Reference Example 1, and the results of the measurement are shown in Table 1 below.

TABLE 1

| Solvent | Permittivity | Solubility (mg/ml) |
|---|---|---|
| Water | 78.5 | Not detected |
| 5% aqueous solution of hydrochloric acid | — | Not detected |
| 5% aqueous solution of sodium hydrogen carbonate | — | Not detected |
| 5% aqueous solution of sodium oxide | — | Not detected |
| Glycerin | 40.1 | 0.0048 |
| N,N-dimethylacetamide | 37.8 | >218 |
| Propylene glycol | 32.01 | 2.3 |
| Ethanol | 24.3 | 0.035 |
| Polyethylene glycol 400 (PEG 400) | 12.5 | 52.04 |
| Benzylalcohol | — | >103 |

As can be seen in Table 1 above, when the tricyclic derivative compound was dissolved in the aqueous solvent, the solubility thereof was not improved even when the pH was changed. In addition, the solubility of the tricyclic derivative compound was not substantially improved even when an organic solvent such as glycerin, propylene glycol or ethanol was used.

When the tricyclic derivative compound was dissolved in an organic solvent such as N,N-dimethylacetamide, dimethylacetamide, polyethylene glycol 400 or benzylalcohol, the solubility thereof was improved, but when water was added to the tricyclic derivative compound to form an injectable formulation, the solubility of the compound was rapidly reduced. The results of the measurement are shown in Table 2 below.

TABLE 2

| Ratio of solvents (PEG 400:water) | Solubility (mg/ml) |
|---|---|
| 0:100 | Not detected |
| 10:90 | 0.00021 |
| 20:80 | 0.00294 |
| 30:70 | 0.001238 |
| 40:60 | 0.05395 |
| 50:50 | 0.18881 |
| 100:0 | 52.04 |

As can be seen in Tables 1 and 2, dissolution solvents having effects on improvement in solubility but harmful to the human body required to be used as solubilizing agents in excessive amounts in order to dissolve the tricyclic derivative compound. However, the use of the solubilizing agents is undesirable because they are harmful to the human body.

TEST EXAMPLE 1

Measurement of Solubility of Lipid Nanoparticles Containing Tricyclic Derivative Compound To measure the solubility of the lipid nanoparticles prepared in Example 1, the following test was performed.

Specifically, 660 mg of the solid-state lipid nanoparticles containing the tricyclic derivative compound, prepared in Example 1, were dissolved by adding 4.0 ml of distilled water thereto. Then, the concentration of the tricyclic derivative compound dissolved in distilled water was measured in the same manner as Reference Example 1. As a result, the solubility was shown to be 10.80 mg/ml.

It was found that the solubility of the tricyclic derivative compound contained in the lipid nanoparticles was increased compared to 0.00 mg/ml which is the water solubility of the tricyclic derivative solubility, measured in Reference Example 1.

In addition, the test results of Reference Example 2 show that the solubility of the tricyclic derivative compound was rapidly reduced when water was added thereto after dissolution using the solubilizing agent, whereas the results of Test Example 1 suggest that the solubility of the tricyclic derivative compound-containing lipid nanoparticles according to the present invention is maintained when water is added thereto.

TEST EXAMPLE 2

Figure 2:
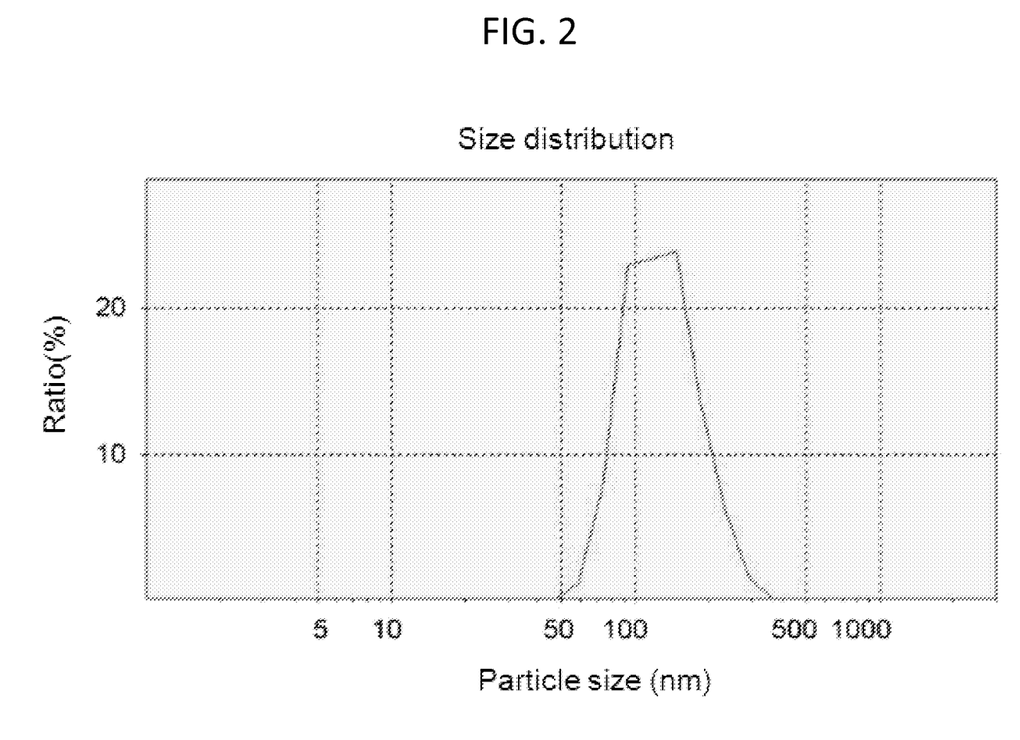
FIG. 2 is a graph showing the results of measuring the size of lipid nanoparticles in one Example of the present invention by a particle size analyzer.

Measurement of Particle Sizes of Lipid Nanoparticles Prepared Using Different Methods for Dispersing Lipid Mixture Solution Containing Tricyclic Derivative Solution The particle sizes of the lipid nanoparticles of Examples 1 to 3 prepared using different methods for dispersing the lipid mixture solution containing tricyclic derivative compound were measured by a particle size analyzer (model: ZETA SIZER-3000, manufacturer: Melbourne), and the results of the measurement are shown in Table 3 below. In addition, the results of measuring the particle size of the lipid nanoparticles of Example 1 are graphically shown in FIG. 2.

TABLE 3

| | Dispersion method | Particle size (nm) |
|---|---|---|
| Example 1 | Dispersing lipid mixture solution by adding water thereto | 103.7 |
| Example 2 | Dispersing lipid mixture solution by adding lipid mixture solution to water | 123.2 |
| Example 3 | Dispersing lipid mixture solution by simultaneously adding lipid mixture solution and water | 107.6 |

As can be seen in Table 3 above, the methods for dispersing the lipid mixture solution containing the tricyclic derivative compound showed a difference of 20 nm or more in the particle size of the prepared lipid nanoparticles, suggesting that the particles of the lipid nanoparticles can be controlled depending on the dispersion method.

TEST EXAMPLE 3

Measurement of Particle Size as a Function of Weight Ratio of Lipid Mixture to Tricyclic Derivative Compound in Lipid Mixture Solution In order to examine the change in particle size of lipid nanoparticles as a function of the change in the weight ratio of the lipid mixture to the tricyclic derivative compound in the lipid mixture solution, the particle sizes of the lipid nanoparticles prepared in Examples 1 and 4 to 9 were measured by a particle size analyzer as described in Test Example 2, and the results of the measurement are shown in Table 4 below.

TABLE 4

| | Weight ratio of lipid mixture:compound of Formula 1 | Particle size (nm) |
|---|---|---|
| Example 1 | 3:1 | 103.7 |
| Example 4 | 2:1 | 125.4 |
| Example 5 | 1:1 | 142.1 |
| Example 6 | 4:1 | 101.1 |
| Example 7 | 6:1 | 94.0 |
| Example 8 | 10:1 | 101.1 |
| Example 9 | 20:1 | 93.4 |

As can be seen in Table 4 below, the particle size of the lipid nanoparticles in the lipid mixture solution was about 90-150 nm, and the particle size of the lipid nanoparticles can be controlled depending on the weight ratio of the lipid mixture to the tricyclic derivative compound. In addition, when the ratio of the lipid mixture to the compound of Formula 1 was less than 3:1, the particle size increased, and when the ratio was more than 3:1, the particle size did not change, suggesting that the optimal ratio of the lipid mixture to the compound of Formula 1 is 3:1.

TEST EXAMPLE 4

Measurement of Particle Size as a Function of Weight Ratio of Ionic Lipid in Lipid Mixture Solution In order to examine the change in particle size of lipid nanoparticles as a function of the change in the weight ratio of ionic lipid in the lipid mixture solution, the particle sizes of the lipid nanoparticles prepared in Examples 1, 10 and 13 to 15 were measured by a particle size analyzer as described in Test Example 2, and the results of the measurement are shown in Table 5 below.

TABLE 5

| | Phospholipid:cholesterol:ionic lipid | Particle size (nm) |
|---|---|---|
| Example 1 | 7:3:1 | 103.7 |
| Example 10 | 7:3:0 | 355.5 |
| Example 13 | 7:3:3 | 159.3 |
| Example 14 | 7:3:5 | 285.1 |
| Example 15 | 7:3:10 | 273.9 |

As can be seen in Table 5 above, the particle size of the lipid nanoparticles can be controlled depending on the weight ratio of ionic lipid in the lipid mixture solution. When the lipid mixture solution contained no ionic lipid, the largest particle size of 355.5 nm was measured, suggesting that the formed lipid nanoparticles re-agglomerated with each other due to the absence of ionic lipid. In addition, when the lipid mixture solution contained at a ratio of 1-10 parts by weight, lipid nanoparticles having a particle size of 103.7-273.9 nm were formed.

TEST EXAMPLE 5

Measurement of Particle Size as a Function of Weight Ratio of Phospholipid in Lipid Mixture Solution In order to examine the change in particle size of lipid nanoparticles as a function of the change in the weight ratio of phospholipid in the lipid mixture solution, the particle sizes of the lipid nanoparticles prepared in Examples 1, 11 and 16 to 22 were measured by a particle size analyzer as described in Test Example 2, and the results of the measurement are shown in Table 6 below.

TABLE 6

| | Phospholipid:cholesterol:ionic lipid | Particle size (nm) |
|---|---|---|
| Example 1 | 7:3:1 | 103.7 |
| Example 11 | 0:3:1 | 130.6 |
| Example 16 | 1:3:1 | 123.3 |
| Example 17 | 3:3:1 | 123.8 |
| Example 18 | 10:3:1 | 108.9 |
| Example 19 | 20:3:1 | 127.0 |
| Example 20 | 30:3:1 | 149.3 |
| Example 21 | 50:3:1 | 170.9 |
| Example 22 | 100:3:1 | 220.7 |

As can be seen in Table 6 above, the particle size of the lipid nanoparticles can be controlled depending on the weight ratio of phospholipid in the lipid mixture solution. When the lipid mixture solution contained no phospholipid, lipid nanoparticles having a particle size of 130.6 nm were formed, and when the lipid mixture solution contained phospholipid at a ratio of 1-100 parts by weight, lipid nanoparticles having a particle size of 103.7-220.7 nm were formed.

TEST EXAMPLE 6

Measurement of Particle Size as a Function of Weight Ratio of Cholesterol in Lipid Mixture Solution In order to examine the change in particle size of lipid nanoparticles as a function of the change in the weight ratio of cholesterol in the lipid mixture solution, the particle sizes of the lipid nanoparticles prepared in Examples 1, 12 and 23 to 27 were measured by a particle size analyzer as described in Test Example 2, and the results of the measurement are shown in Table 7 below.

TABLE 7

| | Phospholipid:cholesterol:ionic lipid | Particle size (nm) |
|---|---|---|
| Example 1 | 7:3:1 | 103.7 |
| Example 12 | 7:0:1 | 169.0 |
| Example 23 | 7:1:1 | 103.8 |
| Example 24 | 7:5:1 | 118.1 |
| Example 25 | 7:7:1 | 133.6 |
| Example 26 | 7:10:1 | 227.8 |
| Example 27 | 7:20:1 | 232.1 |

As can be seen in Table 7 above, the particle size of the lipid nanoparticles can be controlled depending on the weight ratio of cholesterol in the lipid mixture solution. When the lipid mixture solution contained no cholesterol, lipid nanoparticles having a particle size of 169.6 nm were formed, and when the lipid mixture solution contained cholesterol at a ratio of 1-20 parts by weight, lipid nanoparticles having a particle size of 103.7-232.1 nm were formed.

From the results of Test Examples 4 to 6, it could be seen that the optimal weight ratio of phospholipid:cholesterol:ionic lipid is 7:3:1.

TEST EXAMPLE 7

Evaluation of Stability of Lipid Nanoparticles

The lipid nanoparticles prepared in Example 1 were cold-stored while the stability thereof was evaluated. The results of the evaluation are shown in Table 8 below.

TABLE 8

| | Analysis results | | | | | | |
|---|---|---|---|---|---|---|---|
| Item | Date of preparation | After 3 months | After 6 months | After 9 months | After 12 months | After 18 months | After 24 months |
| Appearance (yellow solid powder) | Suitable | Suitable | Suitable | Suitable | Suitable | Suitable | Suitable |
| Purity (HPLC area %) | 99.8 | 99.8 | 99.8 | 99.8 | 99.8 | 99.8 | 99.8 |

As can be seen in Table 8 above, the solid-state lipid nanoparticles were stable in terms of their appearance and purity even after having been stored for 24 months.

TEST EXAMPLE 8

Analysis of Structure of Lipid Nanoparticles

In order to analyze the structure of the lipid nanoparticles prepared in the Examples of the present invention, Cryo-TEM was used.

Figure 3:
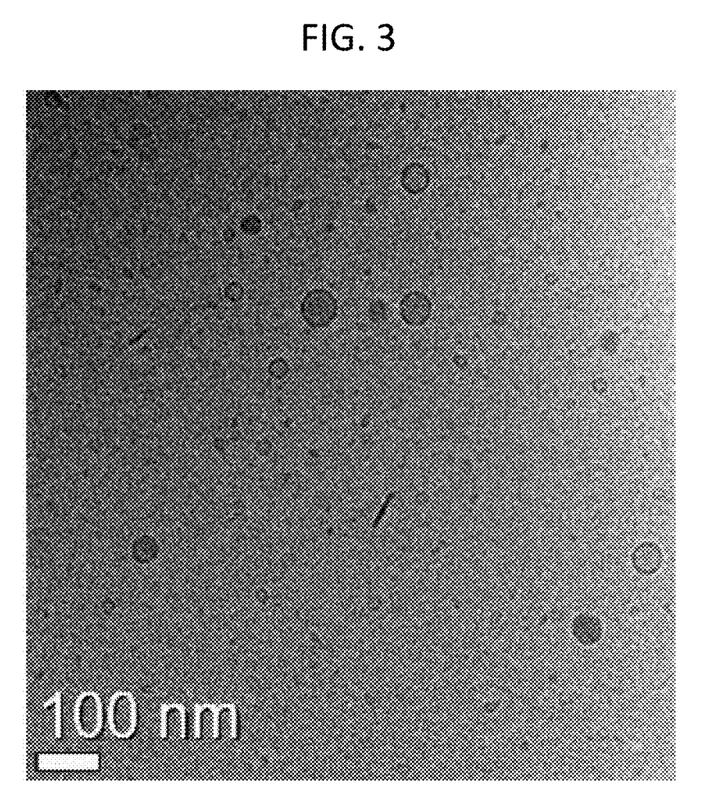
FIG. 3 is a Cryo-TEM image of lipid nanoparticles obtained in one Example of the present invention.
Figure 4:
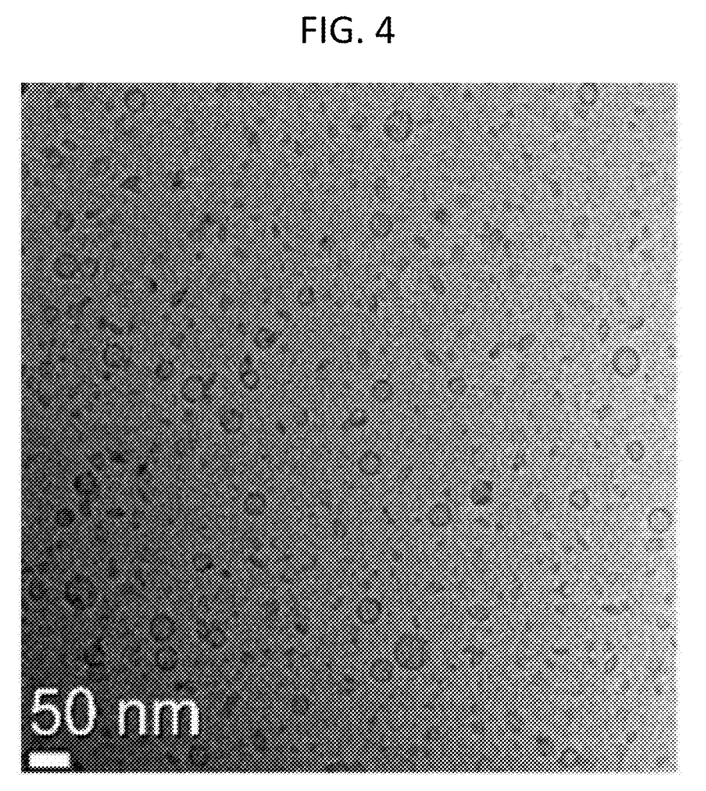
FIG. 4 is a Cryo-TEM image of lipid nanoparticles containing no tricyclic derivative compound, obtained in one Example of the present invention.
Figure 5:
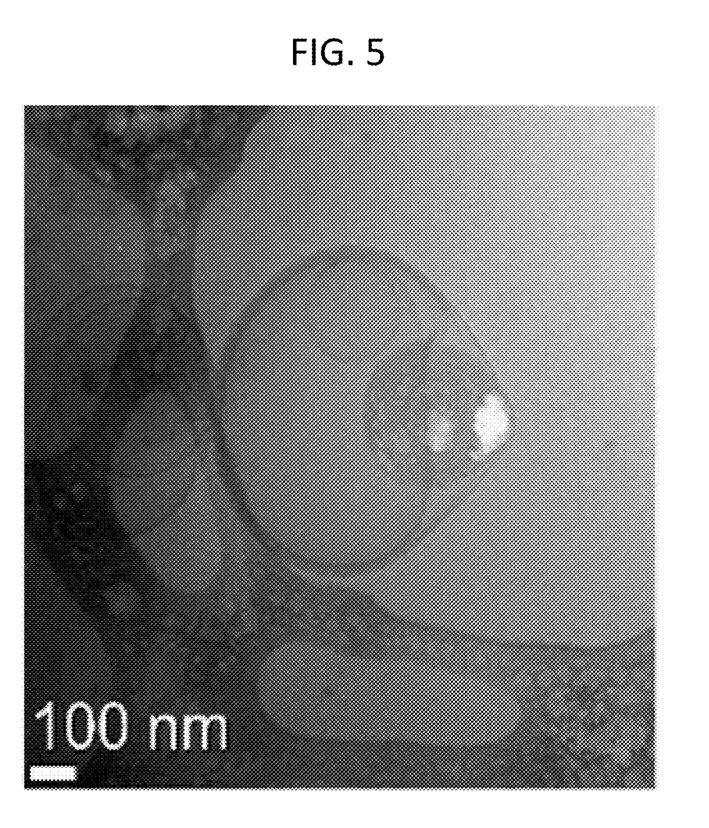
FIG. 5 is a Cryo-TEM image of lipid nanoparticles containing no ionic lipid, obtained in one Example of the present invention.
Figure 6:
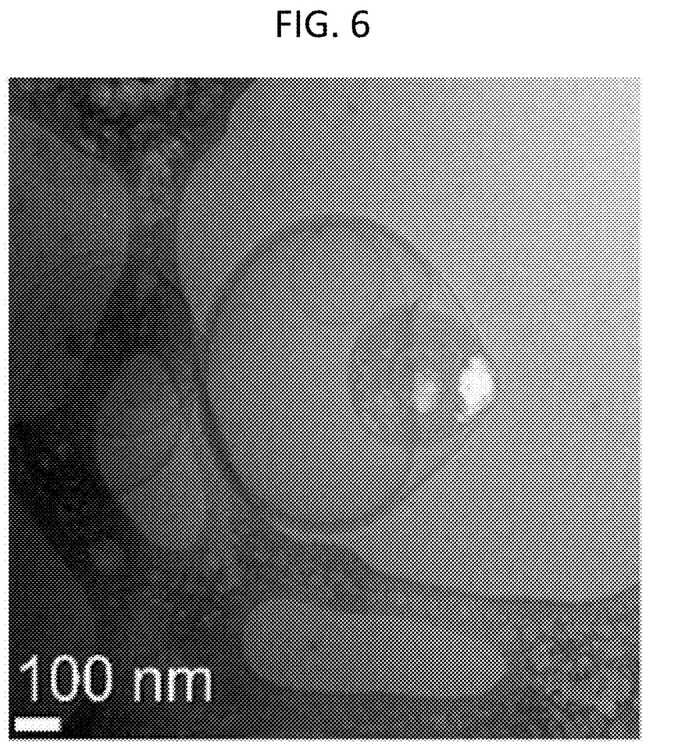
FIG. 6 is a Cryo-TEM image of a tricyclic derivative compound released from lipid nanoparticles containing no ionic lipid, obtained in one Example of the present invention.

Specifically, the structure of the lipid nanoparticles prepared in Example 1 was analyzed using Cryo-TEM (model: Cryo Tecnai F20G2; manufacturer: FEI Company), and the results of the analysis are shown in FIG. 3. Also, FIG. 4 shows the structure of the lipid nanoparticles containing no tricyclic derivative compound, prepared in Comparative Example 1. Moreover, FIG. 5 shows the structure of the lipid nanoparticles containing no ionic lipid, prepared in Example 10. FIG. 6 shows the tricyclic derivative compound released from the lipid nanoparticles prepared in Example 10.

As can be seen in FIGS. 3 to 6, the structure of the lipid nanoparticles was equal between the lipid nanoparticles of Example 1 containing the tricyclic derivative compound and the lipid nanoparticles of Comparative Example 1 containing no tricyclic derivative compound. This indicates that the lipid nanoparticles according to the present invention can stably contain the tricyclic derivative compound. In addition, it could be seen that the lipid nanoparticles containing no ionic lipid, prepared in Example 10, re-agglomerated with each other due to decreased stability, and the tricyclic derivative compound was released from the lipid nanoparticles during the re-agglomeration process.

According to the present invention, lipid nanoparticles are prepared by introducing a lipid mixture to the poorly soluble tricyclic derivative compound of Formula 1 and irradiating the mixture with ultrasonic waves. Thus, the solubility of the tricyclic derivative compound is improved without having to use a solubilizing agent harmful to the human body, and the improved solubility of the compound is maintained even when water is added to the lipid nanoparticles in order to form an injectable formulation. In addition, the solid-state lipid nanoparticles prepared according to the present invention show stability even when they are stored for a long period of time. Thus, the present invention can generally be applied to the preparation of pharmaceutical formulations including the tricyclic derivative compound.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A pharmaceutical composition, comprising:
   lipid nanoparticles consisting of:
      a lipid mixture of hydrogenated soy phosphatidylcholine (HSPC), cholesterol and dipalmitoyl phosphatidic acid (DPPA); and a tricyclic compound of the following Formula 1:

[Formula 1]

wherein the weight ratio of the lipid mixture to the tricyclic compound is 1-20:1.

2. The composition according to claim 1, wherein the lipid mixture is comprised of hydrogenated soy phosphatidylcholine: cholesterol: dipalmitoyl phosphatidic acid at a weight ratio of 7:3:1.

3. The composition according to claim 1, wherein the weight ratio of the lipid mixture to the tricyclic compound is 3:1.

4. The composition according to claim 1, wherein the lipid nanoparticles have a particle size of 1-1,000 nm.

5. The composition according to claim 1, wherein the lipid nanoparticles have a particle size of 20-200 nm.

6. The composition according to claim 1, wherein the pharmaceutical composition is free from solubilizing agent.

7. A method for preparing the pharmaceutical composition according to claim 1, the method comprising:
(1) dissolving in an organic solvent a lipid mixture of hydrogenated soy phosphatidylcholine (HSPC), cholesterol, and dipalmitoyl phosphatidic acid (DPPA) to prepare a lipid mixture solution;
(2) dissolving a tricyclic compound of the following Formula 1 in the lipid mixture solution prepared in step (1),
wherein the weight ratio of the lipid mixture to the tricyclic compound is 1-20:1;
(3) mixing the tricyclic compound-containing lipid mixture solution prepared in step (2) with water while irradiating the mixture with ultrasonic waves to prepare a dispersed lipid nanoparticle solution;
(4) vacuum-distilling the lipid nanoparticle solution, prepared in step (3), to remove the organic solvent; and
(5) freeze-drying the lipid nanoparticle solution prepared in step (4) to prepare the pharmaceutical composition.

8. The method according to claim 7, wherein the organic solvent that is used in step (1) is selected from the group consisting of chloroform, dichloromethane, methanol, ethanol, acetone, acetonitrile, isopropyl alcohol, tetrahydrofuran, and a combination thereof.

9. The method according to claim 7, wherein the lipid mixture in step (1) is comprised of HSPC: cholesterol: dipalmitoyl phosphatidic acid (DPPA) at a weight ratio of 7:3:1.

10. The method according to claim 7, wherein the weight ratio of the lipid mixture to the tricyclic compound in the lipid mixture solution in step (2) is 3:1.

11. The method according to claim 7, wherein dispersion of the lipid nanoparticles in step (3) is performed by 1) adding water to the lipid mixture solution containing the tricyclic compound, 2) adding the lipid mixture solution containing the tricyclic compound to water, or 3) simultaneously adding the tricyclic compound-containing lipid mixture solution and water.

12. A pharmaceutical formulation comprising the pharmaceutical composition of claim 1 and a pharmaceutically acceptable additive.

13. A pharmaceutical formulation comprising the pharmaceutical composition of claim 1 and a pharmaceutically acceptable excipient or adjuvant.

14. An injectable formulation comprising the pharmaceutical composition of claim 1 and a pharmaceutically acceptable excipient or adjuvant.

* * * * *